(12) United States Patent
Berthel et al.

(10) Patent No.: US 6,689,382 B2
(45) Date of Patent: Feb. 10, 2004

(54) SOFT SHELL GELATIN CAPSULES CONTAINING NON-STEROIDAL ANTI-INFLAMMATORIES

(75) Inventors: Alfredo Berthel, Barranquilla (CO); Jorge Gomez, Barranquilla (CO)

(73) Assignee: Procaps S.A., Barranquilla (CO)

( * ) Notice: Subject to any disclaimer, the term of this patent is extended or adjusted under 35 U.S.C. 154(b) by 0 days.

(21) Appl. No.: 10/144,786

(22) Filed: May 15, 2002

(65) Prior Publication Data

US 2003/0219477 A1 Nov. 27, 2003

(51) Int. Cl.$^7$ .............. A61K 9/64; A61K 9/00; A61K 9/48
(52) U.S. Cl. .............. 424/456; 400/400; 400/451
(58) Field of Search .............. 424/400, 1.25, 424/451, 456

(56) References Cited

U.S. PATENT DOCUMENTS 6,383,471 B1 * 5/2002 Chen et al. ............ 424/45
2002/0119200 A1 * 8/2002 Haskell ............ 424/489

* cited by examiner

Primary Examiner—Carlos A. Azpuru
Assistant Examiner—Simon J. Oh
(74) Attorney, Agent, or Firm—Issac A. Angres

(57) ABSTRACT

The present invention provides a pharmaceutical formulation suitable for filling softgel capsules comprising: (a) a therapeutically effective amount of a non-steroidal anti-inflammatory drug selected from the group consisting of selected from the group consisting of (1) the propionic acid derivatives; (2) the acetic acid derivatives; (3) the fenamic acid derivatives; (4) the biphenylcarboxylic acid derivatives; and (5) the oxicams; as well as Cox 2 inhibitors and mixtures thereof; and (b) a solvent system comprising 40% to 60% by weight a polyoxyethylene ether of the formula:

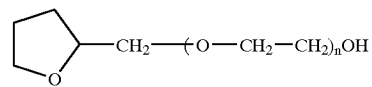

wherein n=1 to 6; 15% to 35% by weight of glycerin and 15% to 35% by weight water. In the case of compositions containing an NSAID having carboxyl function an alkaline hydroxide may be added to neutralize said hydroxide function.

9 Claims, No Drawings

SOFT SHELL GELATIN CAPSULES CONTAINING NON-STEROIDAL ANTI-INFLAMMATORIES

FIELD OF THE INVENTION

This invention relates to stable soft gelatine capsules (hereinafter softgel) containing non-steroidal anti-inflammatory agents (NSAID's) including both cyclooxygenase 1 (Cox1) and cyclooxygenase 2 (Cox2) inhibitors and to a process for the preparation of therapeutically useful, highly stable, soft gelatine capsules, containing non-steroidal anti-inflammatory agents including both cyclooxygenase 1 (Cox1) and cyclooxygenase 2 (Cox2) inhibitors as active ingredients as well as mixtures thereof. The present invention also relates to soft gelatin capsules with a gelatin shell, at least one plasticizer and a capsule filling which contains at least one pharmacologically-active substance and a solvent, as well as processes for their manufacture.

The present invention further relates to a process for solubilizing at least one difficulty soluble pharmaceutical active in a mixture of glycofurol and glycerol and optionally polyvinylpyrrolidone. In further embodiments, the present invention also relates to a process for encapsulating these solubilized pharmaceutical compositions within soft gelatin shells, which are optionally transparent. Both the resulting compositions and their capsules provide an effective means for oral delivery of a wide variety of difficulty soluble pharmaceutical actives.

The instant invention also relates to a liquid softgel fill formulation containing a NSAID and a solvent system containing glycofurol, glycerin, water, optionally polyvinylpyrrolidone and optionally from 0.1 to 1 equimolar amounts of alkaline hydroxide to neutralize the NSAI) when said NSAID contains an acidic moiety.

BACKGROUND OF THE INVENTION AND DESCRIPTION OF THE PRIOR ART

It is well known that liquid, and especially concentrated liquid pharmaceutical compositions offer many advantages over solid compositions. Liquids are easy to swallow and provide an excellent vehicle for the uniform delivery of pharmaceutical actives. Liquids provide a rapid onset of pharmacologic action, since the composition does not first have to disintegrate and dissolve in the gastrointestinal tract. Concentrated liquid compositions are ideally suited for encapsulation within a soft gelatin shell, to provide a portable and easy-to-swallow soft, flexible capsule. Encapsulation would also permit the accurate and uniform delivery of a unit dose of a pharmaceutical active, an advantage which becomes especially important when relatively small amounts of an active are to be delivered. Additionally, soft gelatin capsules are aesthetically appealed (especially when filled with a transparent liquid) and can be manufactured in a wide variety of sizes, shapes, and colors.

Gelatin capsules, especially soft gelatin capsules, have become increasingly important as a medical dosage form since it became feasible, in the 1930's, to manufacture them by making and filling the capsules in one operation. Compared to other medical dosage forms they show many advantages such as being odorless and tasteless, they can be taken easily and, owing to their swelling capability and water solubility, the drugs are readily liberated in the stomach. Numerous drugs which, on account of their instability such as sensitivity to oxidation and to light, their thermal stability or their hygroscopicity, may not be easily processed into other medicinal forms, can be encapsulated without impairment of their function.

The need for encapsulation of pharmaceutically active dosage forms such as liquids, semi-solids, and pastes within a gelatin shell in such a way as to prevent uncontrolled leakage has resulted in the development of a very fundamental pharmaceutical dosage form: the soft gelatin capsule. While a difficult and not particularly accurate process initially, current manufacturing processes for softgels are fully automated, with a high degree of precision.

The softgel (the currently accepted nomenclature adopted by the SoftGel Association) is a one-piece, hermetically sealed soft gelatin shell containing a liquid, a suspension, or a semi-solid.

The most common modern production method involved in the preparation of softgels is a continuous method whereby two gelatin ribbons pass between twin rotating dies. As the ribbons meet, the liquid to be encapsulated is precisely injected between them. The capsule halves are sealed and ejected by the continuous rotation of the dies. See P. Tyle, Specialized Drug Delivery Systems, Marcel Dekker, Inc. (1990) for a general discussion of softgel manufacturing and production technology, in particular, Chapter 10 by Paul K. Wilkinson and Foo Song Hom.

Various gelatin shell masses may be prepared, depending on the fill properties, climatic conditions, and end use. Typically, gelatin formulations include the same basic ingredients, namely, gelatin, plasticizers such as glycerin, water, and optionally preservatives as well as other optimizing ingredients. The formulations of gelatins are well known to those of ordinary skill in the art.

In most cases, the typical rotary die process requires a flowable liquid or fill containing a bio-active ingredient. The fill may be a single phase liquid active, a mixture of miscible liquids, or a solution or a suspension of solids and liquids. Generally, the fill contains glycerin and a medicament. The liquids to be encapsulated in a gelatin shell are also well known to those of ordinary skill in the art.

Many shell and fill formulations are discussed in Van Hostetler and J. Q. Bellard noted below as well as in "Advances in Softgel Formulation Technology", M. S. Patel, F. S. S. Morton and H. Seager, Manufacturing Chemists, July 1989; "Soft Elastic Gelatin Capsules: A Unique Dosage Form", William R. Ebert, Pharmaceutical Technology, October 1977; "Soft gelatin capsules: a solution to many tableting problems", H. Seager, Pharmaceutical Technology, September 1985; U.S. Pat. No. 4,067,960 to Fadda; U.S. Pat. No. 4,198,391 to Grainger; U.S. Pat. No. 4,744,988 to Brox; and U.S. Pat. No. 4,780,316 to Brox. All of the above references are incorporated herein by reference.

Subsequent to the rotary die process used to produce the gelatin shells having a medicament fill therein, the resulting capsules are typically washed with a solvent that evaporates easily. Thereafter, the capsules are typically tumble dried in a series of hollow drums with perforated walls. Heated dry air is continuously pumped through the rotating drums at an air temperature typically less than 35° C. The warm air blown into the capsules appears to penetrate the shell and cause it to dry from the inside by moving the water outward to the surface of the capsule. By the time the capsules exit this process, all of the solvent used in washing has typically been evaporated, and a large proportion (50–60%) of the water from the gelatin shell has been removed. Recent developments in drying include bypassing the drum drying stage and having the capsules dried in a drying tunnel or room as further discussed below.

After the capsules exit the last drying drum, the capsules are typically spread on drying trays. The final drying phase for softgels is typically accomplished by passing the drying trays through drying tunnels or into drying rooms. Stacks of trays are inserted into drying tunnels or drying rooms, in which controlled temperature air (21°–24° C.) and low relative humidity (20–30%) is continuously circulated. Although additional water may be removed from dry capsules by further heating, for example at 40° C., such a procedure has not been found to be practical or necessary. See Van Hostetler and J. Q. Bellard in The Theory and Practice of Industrial Pharmacy, "Capsules", (1970), Chapter 13 at pages 346–383, and in particular at page 380.

The drying time, for most softgels, is 16–24 hours, but may be slightly longer if the softgels are over 20 minims in size or if the softgels contain a non-oily type liquid base. Softgels permitted to come to water equilibrium in this controlled environment are considered "dry". The gelatin fill and shell of such "dry" softgels contain 6–10% water depending on the specific gelatin and fill formula used. After drying, the capsules are typically inspected and finished using varied known techniques.

Soft gelatin capsules serve chiefly for the containment of liquids, i.e. oily solutions, suspensions or emulsions. Vegetable, animal and mineral oils, liquid hydrocarbons, ethereal oils and also polyethylene glycols are in use as fillings. Fats and waxes are also applied or admixed to increase the consistency. Polyethylene glycols are superior to other possible filling materials for soft gelatin capsules in a number of ways. In contrast to oily liquids, polyethylene glycols are mixable with water in all proportions.

At the same time, because polyethylene glycols are able to dissolve many drugs which are sparingly soluble or insoluble in water, the use of polyethylene glycols with such drugs makes possible a particularly favourable liberation of the active material. In many cases, sparingly water soluble drugs which have been dissolved in polyethylene glycols and then put into soft gelatin capsules are outstanding, by virtue of an exceptionally good bio-availability of the drug.

There is always a continuing need for pharmaceutically inert and safe solvents which are able to dissolve larger amounts of active materials and yet can be processed into stable soft gelatin capsules. Solvents suitable for human consumption, such as ethanol, propylene glycol, dimethyl acetamide, lactic acid, glycerol, and butanediol, have been shown by the investigations of the applicant to be unsuitable for introduction into soft gelatin capsules in larger quantities, because the capsule fillings made with these solvents cause, after a short time, softening and deformation of the capsules produced, which therefore are not marketable.

It is also well known that non-steroidal anti-inflammatory drugs (NSAIDs) remain among the most widely prescribed drugs worldwide. A great deal of research in this area has followed Vane's critical discovery in 1971 (Vane JR; Bakhle YS; Botting RM Cyclooxygenases 1 and 2. Annu Rev Pharmacol Toxicol, 1998, 38:, 97–120) that NSAIDs such as aspirin exert their actions primarily by inhibiting the production of prostaglandins (PGs). Cyclo-oxygenase (COX) (also known as PGH synthase or prostaglandin endoperoxide synthase), the key enzyme catalyzing the biosynthesis of PGs, was purified in 1976 and cloned in 1988. A second COX gene was discovered in 1991. It is now known that the two genes express two similar but distinct isoforms of the enzyme—COX-1 and COX-2. The two isoforms have similar primary protein structure (60% homology) and catalyze essentially the same reaction.

Also, a great deal has been learned about the metabolism, regulation, and functions of PGs, the product of COX reaction. Prostaglandins are ubiquitous fatty-acid derivatives that serve as autocrine/paracrine mediators involved in many different physiological processes in addition to their well recognized role in inflammation and immune response modulation. PGs are involved in as diverse normal processes as renal function, vasomotor tone, platelet aggregation and blood clotting, differentiation of immune cells, wound healing, nerve growth, bone metabolism, ovulation, and initiation of labor.

The main pathways by which PGs and other eicosanoids are produced include i.e., tissue damage which activates phospholipase A2 (PL-A2), which causes arachidonic acid to be split off the cell membrane phospholipids. The fate of the released arachidonic acid depends on which of several possible pathways it takes. There are two main pathways; the lipoxygenase pathway leads to the formation of leukotrienes and lipoxins, whereas the COX pathway leads to formation of prostaglandins and thromboxanes.

The two known COX isoforms are similar in size, substrate specificity, and kinetics, but vary in their expression and distribution. COX-1, "the good COX", is a constitutively expressed isoform that is always present in most cells throughout the body and catalyzes the formation of PGs involved in physiological, "housekeeping" processes. In the stomach, COX-1 catalyzes the synthesis of PGE2 and PG 12 that have cytoprotective actions and play an important role in maintaining the integrity of the gastroduodenal mucosa.

COX-2, "the bad COX", is an inducible isoform that is found mainly in inflammatory and immune cells (neutrophils, macrophages, mast cells, etc). Pro-inflammatory cytokines and growth factors induce COX-2, which suggests that it may play an important role not only in the process of inflammation but also in the control of cell growth. At the site of inflammation, COX-2 is responsible for the generation of the hyperalgesic and pro-inflammatory PGs. The de novo synthesis of COX-2 is triggered by the exposure of inflammatory cells to certain stimuli (trigger substances) such as endotoxin, interferon, and cytokines (e.g., interleukin-1) and inhibited by steroids and interleukin-4. COX-2 is also strongly expressed in human colon cancer cells, and NSAIDs are thought to delay the progress of colon tumors possibly by causing apoptosis (programmed cell death) of the tumor cells. The risk of developing Alzheimer's disease, which is thought to involve an inflammatory component, may be reduced by chronic use of NSAIDs. In addition to being inducible, COX-2 is also present constitutively in the central nervous system, where it may be involved in fever and nerve transmission of pain. PGs catalyzed by COX-2 are also involved in ovulation and the birth process.

Approximately 25% of patients using NSAIDs experience some kind of side effect and about 5% develop serious health consequence (massive GI bleed, acute renal failure, etc.). Both COX-1 and COX-2 are inhibited to varying degrees by all currently available (conventional) NSAIDs. Studies published so far support the hypothesis that the undesirable side effects of NSAIDs such gastric erosion and renal dysfunction are due to the inhibition of COX-1, while the anti-inflammatory (therapeutic) effects are due to the inhibition of COX-2.

The inhibitory potency and selectivity of the conventional, 1st generation NSAIDs (aspirin, diclofenac, ibuprofen, indomethacin, naprosyn, and piroxicam, etc) for COX-1 and COX-2 vary greatly. Some NSAIDs (e.g., ketoprofen) are relatively COX-1 selective, some (ibuprofen and naproxen) are essentially non-selective, while others (e.g., diclofenac) are relatively COX-2 selective. Inhibitory effects of NSAIDs on gastric PGE2 synthesis correlate with COX-1 inhibitory potency in blood and with COX-1 selectivity, but not with COX-2 inhibitory potency. However, even COX-2 "selective" NSAIDs still had sufficient anti-COX-1 activity to cause potent inhibition of gastric PGE2. Thus, at therapeutic concentrations, none of the currently marketed NSAIDs spare gastric COX-1 activity.

In general, NSAIDs have comparable efficacy but different safety profiles probably due to differences in their ability to inhibit COX-1 at therapeutic doses. In this respect, the different NSAIDs are evaluated by comparing their IC50 values. The IC50 is the drug concentration that inhibits the activity of the enzyme by 50%. Therefore, the lower the IC50 value the stronger is the drug. This approach is now utilized to study the relative inhibition of the two COX isoforms by a given NSAID. The IC50 values (micromoles/L) for COX-2 and COX-1 are determined in vitro and their ratio is calculated (COX-2 IC50 divided by COX-1 IC50) to provide a quantitative measure of the drug's selectivity. The smaller this ratio the more selective is the drug for COX-2. For example, while the ratios for indomethacin and piroxicam are similar and are about 30, the ratio for the slightly more selective meloxicam is about 0.3. Meloxicam is commercially available in some parts of the world, but not in US. However, at therapeutic doses "preferential" COX-2 inhibitors like meloxicam effectively inhibit both isoforms and therefore undesirable side effects will occur despite the preferential inhibition of COX-2. However, there are currently at least a dozen highly selective COX-2 inhibitors under development by different pharmaceutical companies. These 2nd generation NSAIDs represent a new class of drugs (truly selective COX-2 inhibitors) and are considered a major advance in the management of pain and inflammatory diseases. Of these drugs, celecoxib (SC-58635 or Celebrex by Searle) was the first to gain FDA approval for use in rheumatoid and osteoarthritis. Celecoxib is 375 times more selective for COX-2 relative to COX-1 and, at therapeutic doses, its plasma concentration does not reach the level required for effective COX-1 inhibition. In clinical trials celecoxib showed effective anti-inflammatory activity with virtually no gastrointestinal adverse effects compared to placebo. Other agents under developments, now dubbed "the super aspirins", may have a COX-2 selectivity several fold greater than that of celecoxib with virtually no effect on COX-1 and may therefore afford a much wider margin of safety.

The present invention provides a solvent system for analgesic and non-steroidal anti-inflammatories, Cox 1 inhibitors, Cox2 inhibitors and mixtures thereof, as well as softgel capsules containing such inhibitors. The solvent system is particularly useful for filling soft-gel capsules and the resulting products exhibit good bioavailability and are shelf-stable.

OBJECTS OF THE INVENTION

It is an object of the present invention to provide a new solvent system for Non-steroidal anti-inflammatory compounds.

It is also an object of the present invention to provide a new solvent system useful for filling softgel capsules.

It is a specific object of the present invention to provide solutions containing non-steroidal anti-inflammatories dissolved in glycofurol.

Other objects and embodiments of the present invention will be discussed below. However, it is important to note that many additional embodiments of the present invention not described in this specification may nevertheless fall within the spirit and scope of the present invention and/or the claims.

SUMMARY OF THE INVENTION

The present invention is directed to a pharmaceutical formulation suitable for filling softgel capsules comprising: (a) a therapeutically effective amount of a non-steroidal anti-inflammatory drug selected from the group consisting of Cox 1 inhibitors, Cox 2 inhibitors and mixtures thereof; and (b) a solvent system comprising 40% to 60% by weight a polyoxyethylene ether of the formula:

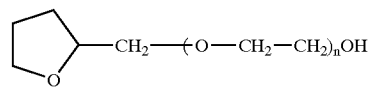

wherein n=1 to 6; 15% to 35% by weight of glycerin and 15% to 35% by weight water.

The present invention also provides a pharmaceutical formulation suitable for filling softgel capsules comprising: (a) a therapeutically effective amount of a non-steroidal anti-inflammatory drug selected from the group consisting of (1) the propionic acid derivatives; (2) the acetic acid derivatives; (3) the fenamic acid derivatives; (4) the biphenylcarboxylic acid derivatives; and (5) the oxicams; and (b) a solvent system comprising 40% to 60% by weight a polyoxyethylene ether of the formula:

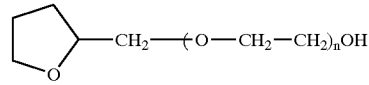

wherein n=1 to 6; 15% to 35% by weight of glycerin and 15% to 35% by weight water.

The instant invention further provides a pharmaceutical soft gelatin capsule in unit dosage form with a filling comprising a non-steroidal anti-inflammatory drug as active ingredient and a solvent system comprising 40% to 60% by weight a polyoxyethylene ether of the formula:

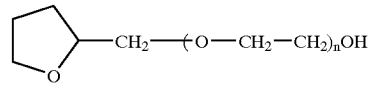

wherein n=1 to 6; 15% to 35% by weight of glycerin and 15% to 35% by weight water.

The invention further provides a pharmaceutical formulation for oral administration having increased stability and bioavailability of an analgesic or anti-inflammatory agent containing a carboxylic acid function, comprising a soft gelatin capsule which essentially contains a therapeutically active amount of said analgesic or anti-inflammatory agent dissolved in a composition comprising: 40% to 60% by weight glycofurol; 15% to 35% by weight of glycerin; 15% to 35% by weight water and an effective amount not to exceed the molar equivalent of the carboxylic acid function of an alkaline metal hydroxide selected from the group consisting of sodium hydroxide and potassium hydroxide.

The instant invention is also directed to a pharmaceutical formulation for oral administration having increased stability and bioavailability of an analgesic or antiflammatory agent, comprising a soft gelatin capsule which essentially contains a therapeutically active amount of ibuprofen dissolved in a composition comprising: 40% to 60% by weight glycofurol; 15% to 35% by weight of glycerin; 15% to 35% by weight water and an effective amount not to exceed the molar equivalent of ibuprofen of an alkaline metal hydroxide selected from the group consisting of sodium hydroxide and potassium hydroxide.

The invention also provides a pharmaceutical formulation for oral administration having increased stability and bioavailability of an analgesic or anti-inflammatory agent, comprising a soft gelatin capsule which contains a therapeutically active amount of a Cox2 inhibitor dissolved in a composition comprising: 40% to 80% by weight glycofurol; 15% to 35% by weight of glycerin; 5% to 15% by weight water.

DETAILED DESCRIPTION OF THE INVENTION

The present invention provides a solvent system for preparing solutions of pharmaceutical agents wherein the prepared solutions are particularly suitable for softgel filling. The pharmaceutical agents suitable for use with the solvent system of this invention are either acidic, basic or amphoteric compounds, i.e., compounds that are readily ionizable.

The present invention provides a solvent system for encapsulating non-narcotic analgesics/nonsteroidal NSAID anti-inflammatory drugs which are known as Cox1 inhibitors, Cox 2 inhibitors as well as mixtures thereof. The particular solvent of interest is based on the polyoxyethylene ethers of tetrahydrofurfuryl alcohol. Of particular interest is a solvent having the following chemical structure

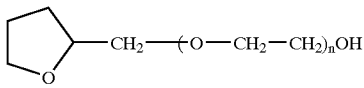

wherein n=1 to 6.

The non-narcotic analgesics/nonsteroidal anti-inflammatory drugs for use in the compositions of the present invention can be selected from the following categories:

(1) the propionic acid derivatives;
(2) the acetic acid derivatives;
(3) the fenamic acid derivatives;
(4) the biphenylcarboxylic acid derivatives; and
(5) the oxicams.

The term "selected NSAID" as used herein is intended to mean any non-narcotic analgesic/non-steroidal anti-inflammatory compound falling within one of the five structural categories but also including aspirin but not acetaminophen and phenacetin.

While some of these compounds are primarily used at the present time as anti-inflammatory agents and others are primarily used as analgesics, in fact all of the contemplated compounds have both analgesic and anti-inflammatory activity and can be used at appropriate dosage levels for either purpose in the compositions and methods of the present invention. The compounds in groups (1) through (4) typically contain a carboxylic acid function; however, those acids are sometimes administered in the form of their pharmaceutically acceptable acid addition or alkali metal salts, e.g., sodium salts.

The propionic acid derivatives for use herein include, but are not limited to, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be encompassed by this group. Presently preferred members of the propionic acid group include ibuprofen, naproxen, flurbiprofen, fenoprofen, ketoprofen and fenbufen.

Thus, "propionic acid derivatives" as defined herein are non-narcotic analgesics/nonsteroidal anti-inflammatory drugs having a free —CH(CH$_3$)COOH or —CH$_2$CH$_2$COOH group (which optionally can be in the form of a pharmaceutically acceptable salt group, e.g.—CH(CH$_3$)COO$^-$Na$^+$ or —CH$_2$CH$_2$COO$^{31}$ Na$^+$), typically attached directly or via a carbonyl function to a ring system, preferably to an aromatic ring system.

The acetic acid derivatives for use herein include, but are not limited to, indomethacin, sulindac, tolmetin, zomepirac, diclofenac, fenclofenac, alclofenac, ibufenac, isoxepac, furofenac, tiopinac, zidometacin, acemetacin, fentiazac, clidanac and oxpinac. Structurally related acetic acid derivatives having similar analgesic and anti-inflammatory properties are also intended to be encompassed by this group. Presently preferred members of the acetic acid group include tolmetin sodium, zomepirac sodium, sulindac and indomethacin.

Thus, "acetic acid derivatives" as defined herein are non-narcotic analgesics/nonsteroidal anti-inflammatory drugs having a free —CH$_2$COOH group (which optionally can be in the form of a pharmaceutically acceptable salt group, e.g., —CH$_2$COO$^-$Na$^+$), typically attached directly to a ring system, preferably to an aromatic or heteroaromatic ring system.

The fenamic acid derivatives for use herein include, but are not limited to, mefenamic acid, meclofenamic acid, flufenamic acid, niflumic acid and tolfenamic acid. Structurally related fenamic acid derivatives having similar analgesic and anti-inflammatory properties are also intended to be encompassed by this group. Presently preferred members of the fenamic acid group include mefenamic acid and meclofenamate sodium (meclofenamic acid, sodium salt).

Thus, "fenamic acid derivative" as defined herein are non-narcotic analgesics/nonsteroidal anti-inflammatory drugs which contain the basic structure

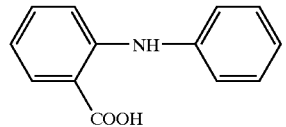

which can bear a variety of substituents and in which the free —COOH group can be in the form of a pharmaceutically acceptable salt group, e.g., —COO$^-$Na$^+$.

The biphenylcarboxylic acid derivatives for use herein include, but are not limited to, diflunisal and flufenisal. Structurally related biphenylcarboxylic acid derivatives having similar analgesic and anti-inflammatory properties are also intended to be encompassed by this group. Preferred members of this group are diflunisal and flufenisal.

Thus, "biphenylcarboxylic acid derivative" as defined herein are non-narcotic analgesics/nonsteroidal anti-inflammatory drugs which contain the basic structure

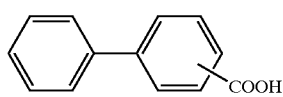

which can bear a variety of substituents and in which the free —COOH group can be in the form of a pharmaceutically acceptable salt group, e.g. —COO⁻Na⁺.

The oxicams for use herein include, but are not limited to, piroxicam, sudoxicam, isoxicam and CP-14, 304. Structurally related oxicams having similar analgesic and anti-inflammatory properties are also intended to be encompassed by this group. A preferred member of this group is piroxicam.

Thus, "oxicams" as defined herein are non-narcotic analgesics/nonsteroidal anti-inflammatory drugs which have the general formula

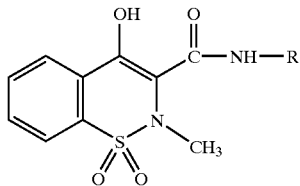

wherein R is an aryl or heteroaryl ring system.

The precise amount of non-narcotic analgesic/non-steroidal anti-inflammatory drug for use in the present compositions will vary depending, for example, on the specific drug chosen, the dosage form thereof, i.e., standard versus sustained release, the condition for which the drug is administered and the size and kind of the mammal.

For humans, typical effective analgesic/anti-inflammatory amounts of presently preferred NSAIDs for use in unit dose compositions of the invention are about 125 to 500 mg diflunisal, about 25 to 100 mg zomepirac sodium, about 50 to 800 mg ibuprofen, most preferably 100–400 mg, about –125 to 500 mg naproxen, about 25 to 50 mg flurbiprofen, and about 50 to 200 mg fenoprofen, about 10 to 20 mg piroxicam, about 125 to 250 mg mefenamic acid, about 100 to 400 mg fenbufen or about 25 to 50 mg ketoprofen; however, greater or lesser amounts can be employed if desired.

The Cox2 inhibitors of the invention are selected from the group consisting of Celecoxib having the formula

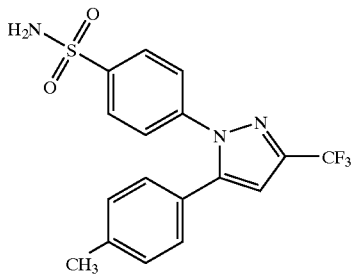

Rofecoxib having the formula

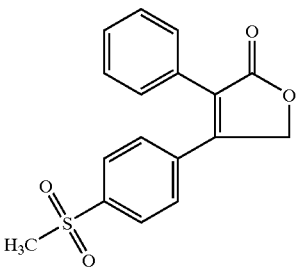

and valdecoxib having the formula

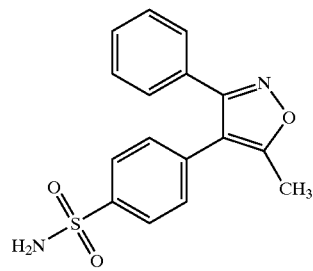

Other Cox2 inhibitors also include Parecoxib and MK 663.

The preferred dosage amounts for the Cox2 inhibitors are 100 mg to 200 mg for Celecoxib; 12.5 mg to 25 mg for Rofecoxib and 5–10 mg for Valdecoxib.

The formulations of the present invention may also include a second pharmaceutical active such as antihistamines, cough suppressants and decongestants. Examples of additional pharmaceutical actives useful in the present invention include, but are not limited to, pseudoephedrine and its salts such as pseudoephedrine hydrochloride; dextromethorphan and its salts such as dextromethorphan hydrobromide; doxylamine and its salts such as doxylamine succinate; phenindamine and its salts such as phenindamine hydrogen tartrate; pheniramine and its salts such as pheniramine maleate; chlorpheniramine and its salts such as chlorpheniramine maleate; ephedrine and its salts such as ephedrine sulfate; triprolidine and its salts such as triprolidine hydrochloride; diphenhydramine and it salts such as diphenhydramine hydrochloride, diphenhydramine citrate, and dephenhydramine 8-chlorotheophyllinate; phenyltoxylamine and its salts; guaifenesin; phenylpropanolamine hydrochloride; and mixtures thereof. Preferred additional pharmaceutical actives are dextromethorphan hydrobromide, doxylamine succinate, pseudoephedrine hydrochloride, chlorpheniramine maleate, guaifenesin, triprolidine hydrochloride, diphenydramine hydrochloride and mixtures thereof.

In the solvent system of the invention, the polyoxyethylene ether solvent of the formula:

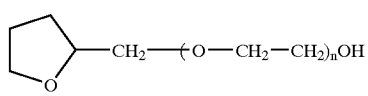

wherein n=1 to 6 is present at a concentration comprising from about 25% to about 65%, more preferably from about 35% to about 60%, and most preferably from about 40% to about 50% by weight. In particular, mixtures in which n=1 to 5 or in which n=1 and 2 are commercially available and suitable for human consumption. Thus the commercial products "Glycofurol 75" (a mixture of mono- and di-ethylene glycol ethers in a ratio of approximately 1:1, with a mean molecular weight of about 168) and Tetraglykol™ (a mixture of mono-ethylene glycol ether, di-ethylene glycol ether and variable proportions of tri-, tetra-and penta-ethylene glycol ethers, with a mean molecular weight of about 190) are especially suitable. A particular preferred polyoxyethylene ether solvent is glycofurol 75.

The solvent system of the invention also includes 5% to 45% by weight glycerin, more preferably about 10% to 40% by weight of glycerin and most preferably 15% to 35% or other similar solvent such as propylene glycol or other low molecular weight polyethylene glycols. The polyethylene glycols useful herein are those which are liquids at room temperature or have a melting point slightly thereabove. Preferred are the polyethylene glycols having a molecular weight range from about 300 to about 1000 and corresponding n values from about 6 to about 20. More preferred are the polyethylene glycols having a molecular weight range from about 400 to about 1000 and corresponding n values from about 8 to about 20. Most preferred are the polyethylene glycols having a molecular weight range from about 600 to about 1000 and corresponding n values from about 12 to about 20. Most especially preferred is a polyethylene glycol having a molecular weight of about 600 and a corresponding n value of about 12. Liquid and low-melting polyethylene glycols are commercially available from Union Carbide (Danbury, Conn.) under the Carbowax™. See Carbowax™ Polyethylene Glycols.

The solvent system further includes 5%–50% by weight water, more preferably 10%–45% by weight water and most preferably 15% to 35% by weight water.

In the cases wherein the NSAID's have a carboxyl or an acidic function, the solvent system of the invention also includes about 0.05–1.0 mole of hydroxide ions for each molar equivalent of the acidic medicine. Hydroxide ions originated, for example, from sodium and/or potassium hydroxide, are used together with water. The most preferred alkaline hydroxide is potassium hydroxide.

The solvent system of the invention may also include optionally 0.5%–25% by weight of polyvinylpyrrolidone (PVP). The soluble forms of polyvinylpyrrolidone are preferred for use in the present invention. Preferred are soluble polyvinylpyrrolidones having an average molecular weight in the range from about 3000 to about 1,000,000; more preferred are those having an average molecular weight in the range from about 7500 to about 50,000; and most preferred are those having an average molecular weight of about 30,000. Moreover, mixtures of two or more soluble polyvinylpyrrolidones of different average molecular weight can be employed.

Other components which can be incorporated into the compositions of the instant invention include colorings, flavorings, preservatives, lubricants, flow-enhancers, filling aids, antioxidants, essences, and other aesthetically pleasing components.

The solubilized pharmaceutical compositions of the present invention can be encapsulated within any conventional soft gelatin shell that is capable of substantially containing the composition for a reasonable period of time. The soft gelatin shells of the instant invention can be prepared by combining appropriate amounts of gelatin, water, plasticizer, and any optional components in a suitable vessel and agitating and/or stirring while heating to about 65° C. until a uniform solution is obtained. This soft gelatin shell preparation can then be used for encapsulating the desired quantity of the solubilized fill composition employing standard encapsulation methodology to produce one-piece, hermetically-sealed, soft gelatin capsules.

In a nut shell, the formation of soft gelatin capsules is carried out in a stamping process wherein the capsule wall is assembled from two gelatin halves which are stamped out of a gelatin band and then molded. Preferably, there is utilized the Scherer process operating under the rotary die method. Herein two endless gelatin bands run against two adjacent and mutually counter-rotating molding rollers. While the gelatin bands are being pressed into the molded and so create the capsule halves, the flowable filler is provided into the thus formed capsule through an exact dosing wedge. There follows the sealing together of the capsule halves, their stamping out, a wash procedure for the freeing of attached oil, a rotational dryer step as well as an adjacent shelf drying.

More specifically, the fill formulation of the instant invention is encapsulated into one-piece gelatin sheath or shell that includes a plasticizer to control the softness and flexibility of the sheath, water, and optionally, other additives, such as flavorants, colorants, opacifiers, etc. The softgel capsules may be produced in a known manner with a rotary die process in which a molten mass of a gelatin sheath formulation is fed from a reservoir onto drums to form two spaced sheets or ribbons of gelatin in a semi-molten state. These ribbons are fed around rollers and brought together at a convergent angle into the nip of a pair of roller dies that include opposed die cavities. A fill formulation to be encapsulated is fed into the wedge-shaped joinder of the ribbons.

The gelatin ribbons are continuously conveyed between the dies, with portions of the fill formulation being trapped between the sheets inside the die cavities. The sheets are then pressed together, and severed around each die so that opposed edges of the sheets flow together to form a continuous gelatin sheath around the entrapped medicament. The part of the gelatin sheet that is severed from the segments forming the capsules is then collected for recycling, and the soft capsules are dried.

Various sheath formulations known in the prior art may be used to encapsulate the fill formulations of the present invention. For example, suitable sheath formulations may include from about 30 to about 50% by weight gelatin; at least 18% by weight, and preferably up to about 40% by weight, of a plasticizer; and from about 20 to about 50% by weight water. These formulations, when formed into capsules and dried, will result in capsule sheaths comprised of from about 40 to about 75% by weight gelatin; from about 18% to about 40% by weight plasticizer; and from about 5 to about 15% by weight water.

The gelatin will normally have a bloom in the range of from about 140 to about 280, and may be Type A or B gelatins or a mixture thereof. Limed bone, acid bone, fish and/or pig skin gelatins may be used.

The gelatin capsules are formed into the desired shape and size so that they can be readily swallowed. The soft gelatin capsules of the instant invention are of a suitable size for easy swallowing and typically contain from about 100 mg to about 2000 mg of the solubilized pharmaceutical active composition. Soft gelatin capsules and encapsulation methods are described in P. K. Wilkinson et al., "Softgels: Manufacturing Considerations", Drugs and the Pharmaceutical Sciences, 41 (Specialized Drug Delivery Systems), P. Tyle, Ed. (Marcel Dekker, Inc., New York, 1990) pp. 409–449; F. S. Hom et al., "Capsules, Soft" Encyclopedia of Pharmaceutical Technology, vol. 2, J. Swarbrick and J. C. Boylan, eds. (Marcel Dekker, Inc., New York, 1990) pp.

269–284; M. S. Patel et al., "Advances in Softgel Formulation Technology", Manufacturing Chemist, vol. 60, no. 7, pp. 26–28 (July 1989); M. S. Patel et al., "Softgel Technology", Manufacturing Chemist, vol. 60, no. 8, pp. 47–49 (August 1989); R. F. Jimerson, "Softgel (Soft Gelatin Capsule) Update", Drug Development and Industrial Pharmacy (Interphex 86 Conference), vol. 12, no. 8 & 9, pp. 1133–1144 (1986); and W. R. Ebert, "Soft Elastic Gelatin Capsules: A Unique Dosage Form", Pharmaceutical Technology, vol. 1, no. 5, pp. 44–50 (1977); these references are incorporated by reference herein in their entirety. The resulting soft gelatin capsule is soluble in water and in gastrointestinal fluids. Upon swallowing the capsule, the gelatin shell rapidly dissolves or ruptures in the gastrointestinal tract thereby introducing the pharmaceutical actives into the physiological system.

The following examples further describe and demonstrate embodiments within the scope of the present invention. The examples are given solely for the purpose of illustration and are not to be construed as limitations of the present invention, as many variations thereof are possible without departing from the spirit and scope of the invention.

EXAMPLES

The following procedure is used throughout the examples below to dissolve the active principle in the solvent system which is then encapsulated in the softgel.

Mix the Glycofurol and the Glycerin under moderate agitation, heat to a temperature ranging from 55° C.+/−5° C. Add the active principle and strongly mix to have a good dispersion. The Potassium Hydroxide was slowly added in an aqueous solution; the mixture is then strongly agitated until a clear transparent solution is obtained. Stop the heating and keep agitating the solution until it is at room temperature. The active material solution is suitable to be encapsulated in soft gelatin capsules.

Example 1

| COMPONENTS | AMOUNT/mg |
| --- | --- |
| Ibuprofen | 200.0 mg |
| Potassium Hydroxide | 24.0 mg |
| Water | 18.0 mg |
| Glycerin | 17.0 mg |
| Glycofurol | 59.0 mg |
| Total | 318.0 mg |

Example 2

| COMPONENTS | AMOUNT/mg |
| --- | --- |
| Ibuprofen | 200.0 mg |
| Potassium Hydroxide | 21.0 mg |
| Water | 23.6 mg |
| Glycerin | 23.0 mg |
| Glycofurol | 50.4 mg |
| Total | 318.0 mg |

Example 3

| COMPONENTS | AMOUNT/mg |
| --- | --- |
| Naproxen | 200.0 mg |
| Potassium Hydroxide | 40.0 mg |
| Water | 18.0 mg |
| Glycerin | 17.0 mg |
| Glycofurol | 59.0 mg |
| Total | 334.0 mg |

Example 4

| COMPONENTS | AMOUNT/mg |
| --- | --- |
| Celecoxib | 200.0 mg |
| Water | 18.0 mg |
| Glycerin | 17.0 mg |
| Glycofurol | 59.0 mg |
| Total | 294.0 mg |

Example 5

| COMPONENTS | AMOUNT/mg |
| --- | --- |
| Rofecoxib | 25.0 mg |
| Water | 18.0 mg |
| Glycerin | 17.0 mg |
| Glycofurol | 59.0 mg |
| Total | 119.0 mg |

Example 6

| COMPONENTS | AMOUNT/mg |
| --- | --- |
| Ibuprofen | 200.0 mg |
| Potassium Hydroxide | 24.0 mg |
| Water | 18.0 mg |
| Glycerin | 17.0 mg |
| PVP Avg. MW 30,000 | 20 mg |
| Glycofurol | 59.0 mg |
| Total | 338.0 mg |

Example 7

Soft Gelatin Capsule Containing a Solubilized Ibuprofen Composition

A soft gelatin mixture is first prepared from the following ingredients.

| INGREDIENT | WEIGHT % |
| --- | --- |
| Gelatin | 48.00 |
| Glycerin | 14.00 |
| Water | QS 100 | the above ingredients are combined in a suitable vessel and heated with mixing at about 65° C. to form a uniform solution. Using standard encapsulation methodology, the resulting solution is used to prepare soft gelatin capsules containing approximately 318 mg of the composition as prepared in Example 1. The resulting soft gelatin ibuprofen capsules are suitable for oral administration.

It is understood that all equivalent features are intended to be included within the claimed contents of this invention. Although the present invention has been described with reference to specific details of certain embodiments thereof, it is not intended that such detail should be regarded as limitations upon the scope of the invention, except as and to the extent that they are included in the accompanying claims.

What is being claimed is:

1. A pharmaceutical formulation suitable for filling softgel capsules consisting of:
   (a) a therapeutically effective amount of a non-steroidal anti-inflammatory drug selected from the group consisting of: (1) the propionic acid derivatives; (2) the acetic acid derivatives; (3) the fenamic acid derivatives; (4) the biphenylcarboxylic acid derivatives; and (5) the oxicams; and
   (b) a solvent system consisting of: 40% to 60% by weight of a polyoxyethylene ether of the formula:

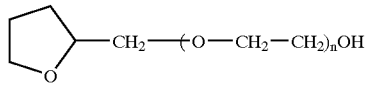

wherein n=1 to 6; 15% to 35% by weight of glycerin and 15% to 35% by weight water; and
   (c) an effective amount not to exceed the molar equivalent of the carboxylic acid function of an alkaline metal hydroxide selected from the group consisting of sodium hydroxide and potassium hydroxide.

2. The formulation of claim 1 wherein said propionic acid derivative is ibuprofen.

3. The formulation of claim 1 wherein said propionic acid derivative is naproxen.

4. A pharmaceutical soft gelatin capsule in unit dosage form with a filling consisting of a therapeutically effective amount of non-steroidal anti-inflammatory drug selected from the group consisting of: (1) the propionic acid derivatives; (2) the acetic acid derivatives; (3) the fenamic acid derivatives; (4) the biphenylcarboxylic acid derivatives; and (5) the oxicams; and a solvent system consisting of: 40% to 60% by weight of a polyoxyethylene ether of the formula:

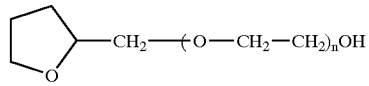

wherein n=1 to 6; 15% to 35% by weight of glycerin; 15% to 35% by weight water; and an effective amount not to exceed the molar equivalent of the carboxylic acid function of an alkaline metal hydroxide selected from the group consisting of sodium hydroxide and potassium hydroxide.

5. The formulation of claim 4 wherein said propionic acid derivative is ibuprofen.

6. The formulation of claim 4 wherein said propionic acid derivative is naproxen.

7. A pharmaceutical formulation for oral administration having increased stability and bioavailability of an analgesic or anti-inflammatory agent containing a carboxylic acid function, comprising a soft gelatin capsule which contains a therapeutically active amount of said analgesic or anti-inflammatory agent dissolved in a composition consisting of: 40% to 60% by weight glycofurol; 15% to 35% by weight of glycerin; 15% to 35% by weight water and an effective amount nor to exceed the molar equivalent of the carboxylic acid function of an alkaline metal hydroxide selected from the group consisting of sodium hydroxide and potassium hydroxide.

8. The pharmaceutical formulation of claim 7 wherein said anti-inflammatory agent is ibuprofen.

9. The pharmaceutical formulation of claim 7 wherein said anti-inflammatory agent is naproxen.

* * * * *